(12) United States Patent
Cuypers et al.

(10) Patent No.: US 7,802,576 B2
(45) Date of Patent: Sep. 28, 2010

(54) HEAD IMMOBILISATION ASSEMBLY FOR PATIENT POSITIONING IN RADIATION THERAPY

(75) Inventors: Steven Cuypers, Gravenwezel (BE); Bogdan Bogdanov, Borgerhout (BE)

(73) Assignee: Orfit Industries, Wijnegem (BE)

( * ) Notice: Subject to any disclaimer, the term of this patent is extended or adjusted under 35 U.S.C. 154(b) by 590 days.

(21) Appl. No.: 11/473,321

(22) Filed: Jun. 23, 2006

(65) Prior Publication Data

US 2007/0010769 A1 Jan. 11, 2007

Related U.S. Application Data

(63) Continuation-in-part of application No. 10/581,596, filed on Jun. 5, 2006, now abandoned.

(51) Int. Cl.
*A61F 5/04* (2006.01)
*A61F 5/37* (2006.01)

(52) U.S. Cl. .................... 128/845; 128/846; 128/859

(58) Field of Classification Search ............... 128/845, 128/846, 857, 869, 870; 5/636–638, 640
See application file for complete search history.

(56) References Cited

U.S. PATENT DOCUMENTS

| | | | |
|---|---|---|---|
| 3,957,262 A | | 5/1976 | McReynolds |
| 4,045,678 A | | 8/1977 | Rickard |
| 4,979,519 A | * | 12/1990 | Chavarria et al. ........... 128/857 |
| 5,081,665 A | | 1/1992 | Kostich |
| 5,370,117 A | * | 12/1994 | McLaurin, Jr. ................. 5/622 |
| 5,531,229 A | * | 7/1996 | Dean et al. ................... 128/866 |
| 5,566,681 A | * | 10/1996 | Manwaring et al. ............ 5/622 |
| 6,376,846 B2 | * | 4/2002 | Livingston ............... 250/492.1 |
| 2002/0108616 A1 | | 8/2002 | Woodburn |

FOREIGN PATENT DOCUMENTS

| | | |
|---|---|---|
| CA | 2222188 | 7/1999 |
| DE | 27911833 | 9/1998 |

* cited by examiner

*Primary Examiner*—Kim M Lewis
(74) *Attorney, Agent, or Firm*—Dykema Gossett PLLC

(57) ABSTRACT

This invention relates to a non-invasive patient immobilisation assembly for immobilising a body part of a patient and for at least temporarily fixing the position thereof. The immobilisation assembly comprises a rigid template (1) made of a thermoplastic material. The template is thermoformed or otherwise moulded in such a way that the inner surface conforms to and contacts the body part to be immobilised along a contact surface area between the template and the body part. The contact surface area corresponds to at least part of the inner surface of the template. The immobilisation assembly also comprises a fixation plate (3, 12, 13) and connecting means (10, 11, 14, 15, 16) for connecting the template (1) to the fixation plate (3, 12, 13) in view of fixing the position of the template and the body part with respect to the fixation plate. The template (1) is provided to exert a fixation force of a preset value to the body part covered by it along the contact surface area by exerting a pulling force pulling the body part towards the fixation plate (3, 12, 13) with the aim of restraining the displacement of the body part within the template within defined limits. The assembly further comprises means (5, 6, 7, 17, 18) for adjusting the fixation force exerted by the template to the preset value.

13 Claims, 2 Drawing Sheets

HEAD IMMOBILISATION ASSEMBLY FOR PATIENT POSITIONING IN RADIATION THERAPY

CROSS REFERENCE TO RELATED APPLICATION

This application is a continuation-in-part of U.S. application Ser. No. 10/581,596, filed Jun. 5, 2006.

FIELD AND BACKGROUND OF THE INVENTION

The present invention relates to a non-invasive patient immobilisation assembly for immobilising a body part of a patient and for at least temporarily fixing the position thereof, wherein the immobilisation assembly comprises a rigid template made of a thermoplastic material, which template is thermoformed or otherwise moulded in such a way that the inner surface conforms to and contacts the body part to be immobilised along a contact surface area which corresponds to at least part of the inner surface of the template, wherein the immobilisation assembly also comprises a fixation plate and connecting means for connecting the template to the fixation plate in view of fixing the position of the template and the body part with respect to the fixation plate, as described in the preamble of the first claim.

Devices immobilising the position of a patients' head or other body part are used to allow for an accurate and reproducible positioning and re-positioning of the body part involved in medical diagnostic imaging and in treatment procedures, as for example in radiation therapy and in surgery. Fractionated treatment (for example MIRT) involves the division of a radiation dose into a multiplicity of sub doses delivered to a patient on different points in time to allow for a maximum recovery of healthy tissue and to minimise complications from overexposure to radiation. In particular when exposing a patients' head to fractionated treatment, precise positioning and highly accurate, reproducible re-positioning of the target and surrounding normal structures of the head is a pre-requisite to ensure that the radiation is delivered exactly at the target position where it is needed, for example a tumor, while minimising the risk to exposure of surrounding healthy tissue.

U.S. Pat. No. 3,957,262 discloses a device for immobilising a patient's head during surgery or examination. The device comprises a headpiece in the form of a cap for receiving and supporting the back of the patient's head that is not to be examined. The interior of the headpiece is made of soft rubber foam which conforms to the size and shape of the back of the patient's head to be supported by it. The patient's head is restrained in a certain position within the cap by means of a chin restrainer and forehead restrainer. The restrainers take the shape of a band, both ends of which are fastened to opposite sides of the hole containing the head. The bands extend over a part of the face, provide a local fixation only and still permit moving of eyes, nose, lips, cheeks etc, thus the parts that have to be subjected to treatment. Because of the limited size, a high local tension will be sensed by the patient's face at the position of the bands. The device further comprises means for changing the distance between the headpiece and the surface supporting the headpiece and the patient. However, there is no indication in U.S. Pat. No. 3,957,262 that the material, of which the cap, chin and forehead restrainer are made, is transparent to irradiation. U.S. Pat. No. 3,957,262 does not recognise the need to an accurate re-positioning of the head which is to be subjected to treatment. U.S. Pat. No. 3,957,262 does not recognise the problem that the dimensions of the head may vary in the course of the fractionated treatment, and does not provide the means to adapt the shape and dimensions of the cap accordingly. This is particularly important with fractionated treatment and irradiation of the head or face, which should be carried out with the best obtainable reproducibility.

DE-U-279.11833 teaches to configure the position of a patient with respect to a supporting surface, by means of a radiation transparent shield covering the patient. A plurality of inflatable cushions are mounted to the inside of the shield. In the inflated state, the cushions configure the position of a patient. However, DE-U-279.11833 does provide the means which permit a reproducible positioning of the patient over longer periods of time associated with fractionated treatment, where days, weeks or more may lapse between subsequent treatments. The reason is that the cushions are re-inflated before every treatment. If the body takes a slightly different position as compared to a previous treatment, this will be taken over by the cushions upon inflation.

U.S. Pat. No. 5,370,117 discloses a patient immobilisation system for repeated use in imaging and treatment of brain tumors, comprising an immobilisation plate onto which a positioning mask is to be fixed. On opposite sides of the immobilization plate a pair of side rails are mounted, studs protruding from the outer face of the side rails. The mask is formed over the head of the patient, holes provided along the side edges of the mask are slipped over the studs. The mask is held in place against the side rails by means of a pair of anchor bars having a multiplicity of holes adapted to engage the studs. Thus, the lower ends of the mask are received between the outer face of the side rails and the anchor bars. To prevent the mask from wobbling from side to side, the lower ends of two vertical leg portions of a relatively rigid arc are secured to the outer edge of the anchor bars, the apex of the arc being connected to an upwardly disposed flap of the mask. Between the pair of side rails, a head and neck support may be slideably mounted. This immobilisation system is however only concerned with improving the accuracy of the mask positioning with respect to the immobilisation plate, but does not address the problem of restraining the movability of the patient's head within the contours of the mask, nor is it concerned with the reproducibility of the patient positioning in fractionated treatment.

US2002/108616 discloses an invasive patient immobilisation system, comprising a mouth piece fixation member to be received within the patient's mouth, and a thermoplastic mask which is formed to the patient's face by placing the softened thermoplastic material across the patient's face, in such a way that it also extends over the mouth piece fixation member. While the thermoplastic mask is left to cool and harden, a fastener plate is coupled to the mouth piece fixation member to fix it to the thermoplastic mask. Following cooling, the mask reflects the contours of the patients face. However, the presence of the additional member in the mouth is uncomfortable to the patient and adds an additional member which may hamper irradiation. Similar to the above discussed prior art publications, US2002/108616 does not address the problem of restraining the movability of the patient's head within the contours of the mask, nor is it concerned with the reproducibility of the patient positioning in fractionated treatment.

U.S. Pat. No. 5,566,681 discloses a non-invasive device for stabilising or immobilising a specific body part to a support frame. The device comprises a rigid thermoplastic template, which provides a personal fit for the support and stabilisation of the body part to be immobilised. The template is obtained by softening the thermoplastic sheet, forming it to the body part to be immobilised, and cooling it to confine it into the moulded shape. The rigid template may include a plurality of fiducial markers affixed to it, to provide reference points for guidance during surgery. Thus the need can be overcome to apply fiducial markers to the body part or to a positioning apparatus. However, once moulded to the body part, the thermoplastic template cannot take account of any changes that have been occurred with the size or shape of body part that needs immobilisation. Shrinking of the body part following weight loss, will result in a fitting of the template which is insufficiently tight and allows the patient to move within the template; growing of the body part to be immobilised will result in a too tight, uncomfortable fit. Remoulding is not an option as the position of the fiducial markers after remoulding will not conform to the original position.

There is thus a need to an immobilisation device which goes beyond envisaging a precise positioning of the body part with respect to a diagnostic or treatment device for one single time. In particular there is a need to an immobilisation device which allows for a precise and reproducible re-positioning of each part of a body part with high accuracy, even in case of fractionated treatment where time intervals of varying duration may elapse between subsequent treatments, which provides the desired comfort to the patient and does not exert excessive local pressure, and which allows to take account of varying dimensions of the body part involved in the course of a fractionated treatment while maintaining the required standards of the accuracy and reproducibility required when re-positioning the body part with respect to the treatment device. A precise positioning of the target position and surrounding normal structures of the body part with respect to the diagnostic/treatment irradiation devices is essential to ensure that exposure is limited to the envisaged tissue and the risk to damaging surrounding healthy tissue is minimised.

It is therefore the object of the present invention to provide a non-invasive immobilisation device with which a precise and reproducible positioning and re-positioning of the patients' body part to be treated may be achieved in the course of fractionated treatment or examinations, even when occurring after time intervals of varying lengths and with varying dimensions of the body part over the treatment period and which at the same time provides improved comfort to the patient.

It is a particular object of this invention to provide a non-invasive immobilisation device with which a precise re-positioning of the patients' head can be achieved, with varying dimensions of the head, without this going at the expense of comfort to the patient.

SUMMARY OF THE INVENTION

This is achieved according to the present invention, by an immobilisation assembly characterised by a template which is provided to exert a fixation force of a preset value to the body part covered by it along the contact surface area, by exerting a pulling force pulling the body part towards the fixation plate along the contact surface area, with the aim of restraining the displacement of the body part within the template within defined limits, the assembly further comprising means for adjusting the fixation force exerted by the template to the preset value.

The inventor has found that when pulling the body part to be immobilised towards the fixation plate, a normal fixation force $F_N$, which extends perpendicular to the template, is exerted to the body part. This normal fixation force has the effect of improving the stability of the immobilisation assembly and of decreasing the risk to a horizontal and rotational displacement of the body part even in case horizontal or rotational forces are applied to the body part. Using the suitable value of the normal fixation force $F_N$ during the whole period of irradiation treatment increases the stability of the fixation and improves the precision with which the patient may be positioned and re-positioned in the same way, even with long time intervals between subsequent treatments, while optimising comfort to the patient. Thereby $F_N$ is preferably maintained constant in subsequent treatments, but if necessary it may be varied. The immobilisation device of this invention provides suitable balance between sufficient stability and optimum fixation, precise positioning and improved comfort of the patient.

An analysis of the problems occurring with existing fixation devices has revealed that at current techniques exist which permit to achieve a precise positioning of the fixation or support plate which supports the patient with respect to the medical diagnosis or treatment device. The template, fixes the position of the body part while laying on the fixation plate. The template is made of thermoplastic material which is moulded to the body part to take the shape of the body part, by heating the thermoplastic material to the molten state. When in the molten state, the thermoplastic material is applied to cover the body part to be treated, for example the head, moulded by shaping it to follow the contours of the body part as closely as possible, fixed to the fixation plate at three or more positions and allowed to cool on the body part e.g. the patients' face for approximately 10 minutes. This transfers the shape of the body part to the template, in such a way that at least part of the inner surface of the template contacts the body part, thus forming a contact surface. The contact surface area may be equal to or smaller than the inner surface of the template. During cooling and crystallisation a shrinking of the thermoplastic material takes place, which can be associated with a volume contraction as a result of which the inner surface template fits well to the patients' face and follows its shape and the shape of the parts present on it and its skin, along the contact surface area between the template and the face. Thereby the contact surface area may but must not increase. However, depending on the nature of the thermoplastic material used, the fitting of the template may become too tight when the thermoplastic material has fully cooled down, or it may become or too loose after a while with shrinking dimensions of the body part.

The inventor has also observed that upon storage of a thermoplastic template for several hours or days at room temperature after having been moulded, annealing of the thermoplastic material takes place during which the thermoplastic material shows further shrinking. The annealing is often associated with additional shrinking, the degree of shrinking depending on the nature of the material, as well as on the geometrical size and design of the polymer sheet used to make the template. When applied to the patients' head and face after having been moulded a few days ago, as a result of the additional shrinking occurred during annealing, often the template fits too tightly to the face, thus rendering the contact between the inner surface of the template and for example the patients' face along the contact surface area uncomfortable. This is unwanted.

The inventor has further observed that in the course of time the body part may shrink when the patient is loosing weight, or increase when the patient is gaining weight, or shows swelling for other reasons. This has the consequence that either the contact between the inner surface of the template and the body part will be at least partly lost and the patient will be able to move the body part within the template which goes at the expense of the accuracy of the positioning of the body part within the template, or that the fitting of the template along the contact surface area will become more and more tight and less comfortable.

It is therefore a particular object of this invention to provide an immobilisation device which provides optimum positioning, fixation and comfort to the patient, even with varying dimensions of the body, with respect to a fixation plate and an external irradiation device. Once insight in these problems had been obtained, it became clear that the problem of a too tight fitting as well as the problem of a too loose fitting of the inner surface of the template to the contours of a body part could be solved by making use of an assembly comprising (a) a template the inner surface of which is provided to exert a pulling fixation force of a pre-determined magnitude to the body part of the patient that is to be treated, along the contact surface area and (b) means which permit adjusting the fixation force exerted by the template to the body part along the contact surface area.

The fixation force is arranged to pull the part of the patient to be treated towards the support or fixation plate along the contact surface area, in view of restraining the displacement of the body part as well as the whole surface of the body part that needs to be treated within the template, to achieve a high stability of fixation and a fixation with a high precision. By using a template which applies and averages fixation forces over a larger contact surface area, which minimises the risk to local over pressure. Because of the presence of means for adjusting the pulling force, the fixation force exerted by the template along the contact surface area may be kept virtually constant during repeated and subsequent treatments, even with varying dimensions of the body part from one treatment to the next, after a time interval has expired. This permits maintaining the stability of the immobilisation device, as well as positioning and fixation precision, combined with improving comfort to the patient.

The presence of means for varying the fixation force also permits re-using a template that has been made once to fit to the shape of the body part, for an infinite number of times, even in case the body part shrinks or grows in the period of time between subsequent treatments. The period of time between subsequent treatments may vary in length from days pr weeks or more. In case of too tight fitting (higher value of the normal fixation force $F_N$), comfort to the patient may be improved by increasing the distance between the template and the fixation plate, over a small distance of for example 0.05-0.5 mm, with provides somewhat more room to the body part without this going at the expense of the accuracy of the patient's position or of the restraints imposed to the displaceability of the body part, since the same suitable preset value of the normal fixation force $F_N$ is applied on the body part by the immobilization assembly.

In a preferred embodiment of the invention, the option is provided to keep the fixation force along the contact surface area constant during subsequent treatments or to vary the fixation force to a pre-defined value. Re-positioning of the body part in fractionated treatments where days or weeks or more may lapse between subsequent treatments, may be achieved with high accuracy and reproducibility. Thus the device of this invention allows for a selective treatment irradiation and examination of the target position, while leaving surrounding normal structures of the patient unaffected. Especially when treating the head, a precise positioning is essential, as a slightly wrong positioning may involve the loss of essential functions within the brain tissue.

In general, it is preferred that the fixation force exerted by the template is about 75-200 N, preferably 100-150 N, as within this range a good compromise is provided between the reproducibility of the patient positioning, the stability of the template with respect to the fixation plate and comfort to the patient and sufficiently restraining the ability of the body part to move within the template, without other invasive or non-invasive parts being mounted to the template. Depending on the part of the body to be treated, this force may be increased or reduced. Typically, to be comfortable while reducing the risk to adversely affecting the accuracy of the patients position, the fixation force may be adjusted such that a movement of maximum approximately 0.5-1.5 mm as requested by the technical field is allowed, to improve comfort to the patient. This may be particularly relevant when irradiating the head. With the templates used at present, the patient often has the possibility of moving his body part over a distance of between 1.5-5 mm or more, which puts the results of the radiation therapy at risk.

An optimum application of the pulling force has been found to occur if the pulling force is exerted to the edges of the template, in particular the edges along which the template is connected to the fixation plate. This will pull the whole template to the body part and the fixation plate, will increase the contact surface area and the fixation forces will be distributed and averaged over a larger contact surface area thus improving comfort to the patient. The preset pulling force may be exerted to the edges, either directly or indirectly through the connecting means connecting the template to the fixation plate.

Another preferred embodiment of the immobilisation assembly of this invention is characterised in that the means for adjusting the pulling force exerted by the template comprise means for varying the distance of the template with respect to the immobilised part of the patient. This may be achieved by any suitable means known to the man skilled in the art and allows to control the magnitude of the force exerted by the template, to adjust this force in subsequent treatments and keep it virtually constant in view of providing high stability and reproducibility of the patient positioning and comfort.

Still another preferred embodiment of this invention is characterised in that the means for adjusting the pulling force exerted by the template comprise means for displacing the patients' head with respect to the template.

The invention and additional preferred embodiments are further elucidated in the appending figures and description of the figures.

DETAILED DESCRIPTION OF THE PREFERRED EMBODIMENTS

Figure 1:
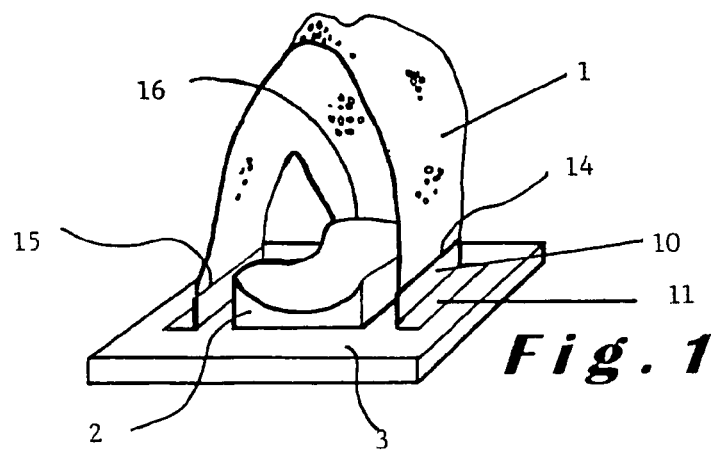
FIG. 1 is a view to a preferred embodiment of the assembly of this invention.

The embodiment of the assembly of this invention shown in FIG. 1 comprises a template 1, the position of which is fixed by connecting it to a fixation plate 3. In the embodiment shown, the template 1 is provided to cover at least part of the head of a patient. Thereby the inner surface of the template contacts at least part of the surface of the body part that needs to be immobilized and defines the contact surface area between the two. However, the template may be designed to cover the entire face or head or to partially or fully cover any other body part of a human being or an animal.

The template 1 shown in FIG. 1 is preferably made of a thermoplastic material, which is moulded by positioning the patients' head onto the fixation plate. If so desired, to improve comfort to the patient and to improve the patient positioning and reproducibility thereof, the head and neck may be supported by a head and neck support 2.

For the sake of simplicity and because of the particular importance of an accurate positioning when treating the head of a patient, hereafter reference will be made to a template for fixing the position of the face of a patient. To achieve a positioning of the body part of the patient to be treated/examined by irradiation which is as accurate as possible, even with fractionated treatment, the template 1 is directly moulded to the surface of the patients' face to be treated. When moulding the template, the thermoplastic material is heated to the molten state, where the thermoplastic material becomes sufficiently flexible and deformable or mouldable to be shaped over the patients' face. When molten, the thermoplastic material is applied to the patients' face and shaped to follow the contours of the face, i.e. nose, cheeks, chin, eyes, mouth etc. in such a way that a contact area is established between the template and the patients' face with is as large as possible. The opposite longitudinal edges 14, 15 of the template 1 which extend along the patients' head, as well as the transversal edge 16 which extends along the top of the patients' head are fixed to the fixation plate 3.

Figure 2:
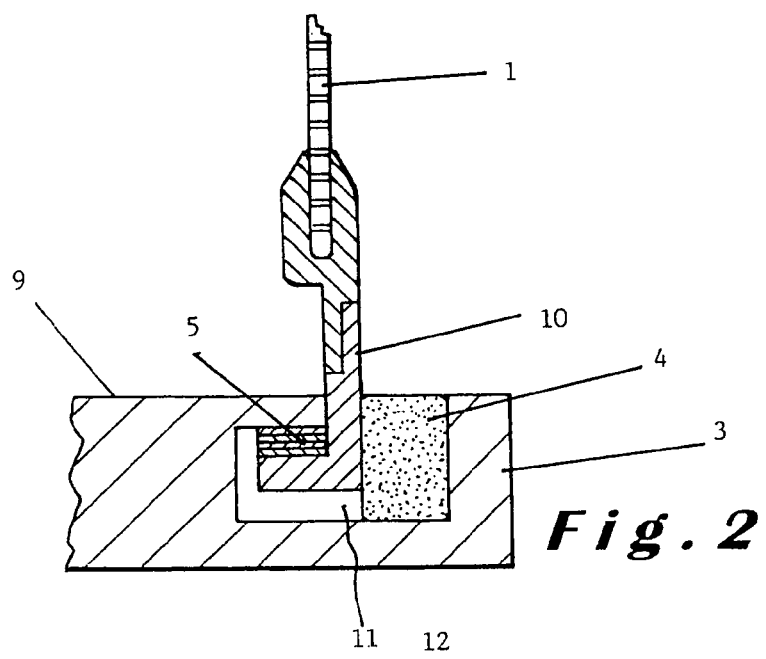
FIG. 2 is a cross section of the assembly of this invention, showing the fixation of the template to the fixation plate in the presence of a spacer.

To fix the template 1 to the fixation plate 3, as is shown in FIG. 2, to the opposite longitudinal 14, 15 and transversal 16 edges of the template each time a rail 10 is connected, which is provided to co-operate with a corresponding groove 11 provided in the fixation plate 3. However, any other suitable connecting means known to the person skilled in the art for connecting the template 1 to the fixation plate 3, may be used. Also, if so desired the template 1 may be fixed to the fixation plate at any other position or at additional positions. Usually the nature and position of the connecting means will be adapted depending on the nature of the body part to be immobilised by the template 1. Besides the direct fixation of the template to the fixation plate, also an indirect fixation may be used, for example in case an intermediate supporting surface is positioned between the template and the fixation plate. The fixation plate may take the form of a separate device, but may for example as well be a support surface.

The template 1 is allowed to cool on the patients' face to allow for a crystallisation of the thermoplastic material, for approximately 10 minutes. The cooling and crystallisation of the thermoplastic material have been found to be associated with a volume contraction of the material as a result of which the template shrinks and its inner surface fits well to the patient's face and a contact surface area is formed between the template and the patient's face. As a consequence of this shrinking the length of the material extending between the opposite longitudinal edges 14, 15 of the template 1 is reduced and a force is exerted to the patients' face along the contact surface area. Fixation forces are distributed and averaged over the contact surface area and the risk to local over pressure is reduced to a minimum. Depending on the nature of the thermoplastic material used, the fitting of the template may be either insufficient and allow for a displacement of the patients' head within the template, or become too tight. Also, when stored for some more time at room temperature, annealing of the material takes place which has been found to be associated with a further shrinking of the template due to the complete crystallisation and re-crystallisation of the thermoplastic material. The additional shrinking has the consequence that there is a risk that the template fits too tightly to the patients' face along the contact surface area, which is uncomfortable.

Therefore, with the present invention means are provided with which the template 1 may be provided to exert a pre-determined force to at least part of but preferably the whole surface of the part of the patient covered by the template 1 along the contact surface area, in view of pulling the immobilised part of the patient towards the fixation plate 3 along the contact surface area and of restraining the displacement of the body part and its surface immobilised within the template 1. As a large contact surface area is present between the inner surface of the template and the surface or skin of the body part, and the pre-determined normal pulling force $F_N$ is averaged over the contact area which increases comfort to the patient. The pulling force is preferably adjustable so as to allow increasing or reducing it depending on the specific circumstances. Thereto means are provided which allow adapting the pulling force exerted by the template either in a continuous or a discontinuous manner, for example in discrete steps. If so desired however, the means may be provided to exert a pulling force the value of which is adjustable or may take different values.

To allow adjusting the pulling force exerted by the template 1, the assembly of this invention may comprise a device for measuring the pulling force. The assembly of the present invention may further comprise means 2, 5, 6, 7, 10, 11, 12, 13, 14, 15, 16 for adjusting the position or distance of the template 1, the fixation plate 3 and/or the head and neck support 2 with respect to each other. It is preferred that the distance varying means are adjustable in such a way that a virtually constant pulling or fixation force may be applied by the template 1 to the patients' head, to ensure optimum reproducibility of the patient positioning not only within the template but also with respect to the fixation plate 3 and medical diagnostic or treatment device, and at the same time maximising patient comfort. The distance varying means may either be continuously adjustable as for example shown in FIG. 4, 5, 6, or may be adjustable in discrete steps by means of a spacer 5, 20 as is shown in FIG. 2, 3.

The pulling force exerted by the template 1 is preferably varied by varying the distance between the template and the patients' head which is supported by the fixation plate 3 and/or head and neck support 2. This distance may be varied by providing means with which either 1. the distance of the template 1 with respect to the fixation plate 3, 12, 13 may be varied, i.e. positioning the template 1 in a moveable manner with respect to the fixation plate 3, 12, 13;
2. the position of the fixation plate 3, 12, 13 with respect to the template 1 may be varied. If use is made of a head and neck support 2, this will usually have the consequence that also the position of the head and neck support 2 with respect to the template 1 is varied.
3. the position of the head and neck support 2 with respect to the template 1 may be varied, i.e. positioning the head and neck support 2 in a moveable manner or moveably positioning either the fixation plate 3 or the template 1 with respect to the head and neck support 2
4. the position of the template 1 and fixation plate 3 with respect to the head and neck support 2 may be varied.

However, also any combination of the above described features may be used, depending on the envisaged use of the assembly.

As is shown in FIG. 2, the pulling force exerted by the template 1 and the position of the template with respect to the fixation plate 3 may for example be varied by varying the position in height direction of the device, in which the rail 10 is inserted in the groove. When inserted lower in the groove 11, further away from the support surface 9 supporting the head, the pulling force will be increased. When inserted closer to the support surface 9, the pulling force will be decreased. The positioning of the rail 10 within the groove 11 may for example be varied by using spacers 5, taking the form of inserts which are to be inserted in the groove 11 or removed therefrom. Any space remaining in the groove 11 may be filled with an additional member 4.

Figure 3:
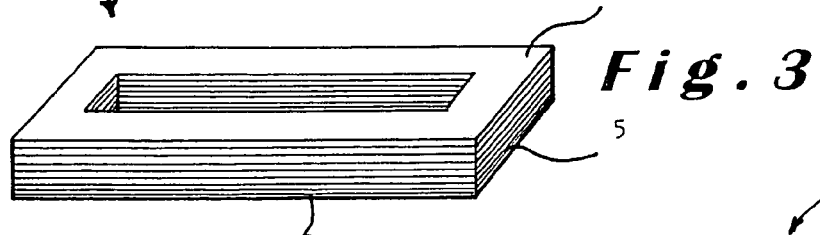
FIGS. 3, and 4 show a view to a fixation plate comprising a top and bottom face which are spaced from each other using different types of spacers.

In the embodiment shown in FIG. 3, either the head as such or the head and neck support 2 is provided to be positioned on top of a spacer 20, positioned on top of the fixation plate 3. The spacer 20 comprises a plurality of super imposed plates 5. The thickness of the spacer, and thus the distance between the fixation plate 2 and the template may be varied by adding or subtracting one or more plates 5. By increasing the number of plates 5, the force applied by the template 1 to the patients head may be increased. By decreasing the number of plates, the force applied by the template to the patients head may be decreased. Usually lifting or lowering of the patients head by approximately 0.05-0.5 mm, preferably 0.1-0.3 mm will be sufficient to release a too tight force or to increase the force applied by the template. However, depending on the part of the patient to be treated, this distance may be smaller or larger. As can be seen from FIG. 3, the spacer 20 may be hollow in the centre, so that the patient may be irradiated from all directions with minimum loss of radiation intensity.

Figure 4:
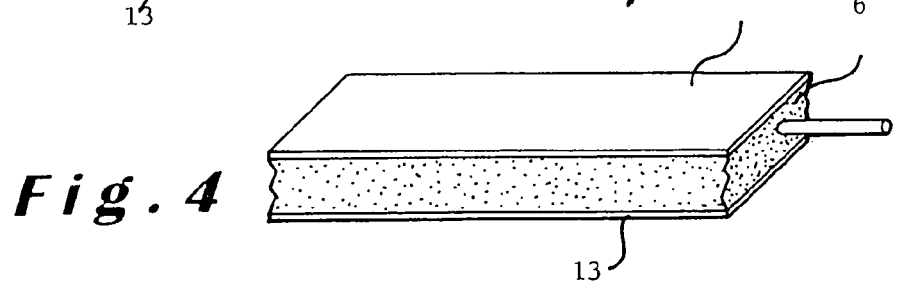

In the embodiment shown in FIG. 4, the fixation plate comprises an upper and a lower surface 12, 13 which are spaced from each other by means of a spacer, which in this case is formed by an expandable member 6. The height of the expandable member 6 is variable. By expanding or contracting the member, the patient will be moved towards and from the template, thus increasing or reducing the force exerted by the template to the patients' head. Expansion or contraction of the member 6 may be achieved in any suitable manner known to the man skilled in the art, for example in a pneumatic or a hydraulic manner. However, the device 19 shown in FIG. 4 may also be used as a spacer which is provided for positioning between the fixation plate 3 and the head and neck support 2.

Figure 5:
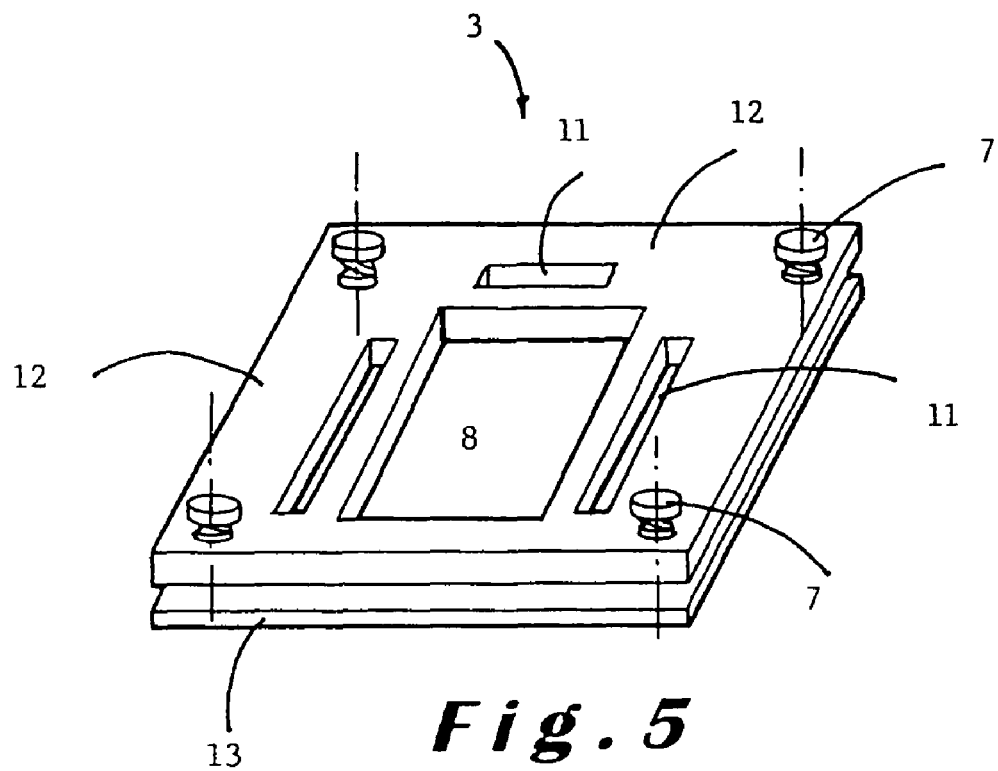
FIGS. 5 and 6 are detailed views to a fixation plate comprising a top and bottom face which are spaced from each other using adjustable spacers.

In the embodiment shown in FIG. 5, the top and bottom surface of the fixation plate 3 are displaceable to and from each other by means of a spacers 7 having a continuously variable height. In the embodiment shown in FIG. 5, the top surface 12 of the fixation plate is provided for receiving the connecting means for connecting the template to the fixation plate, whereas the head and neck support is provided to be positioned in the cavity 8 provided in the top surface 12, and to be supported by the bottom surface 13.

Figure 6:
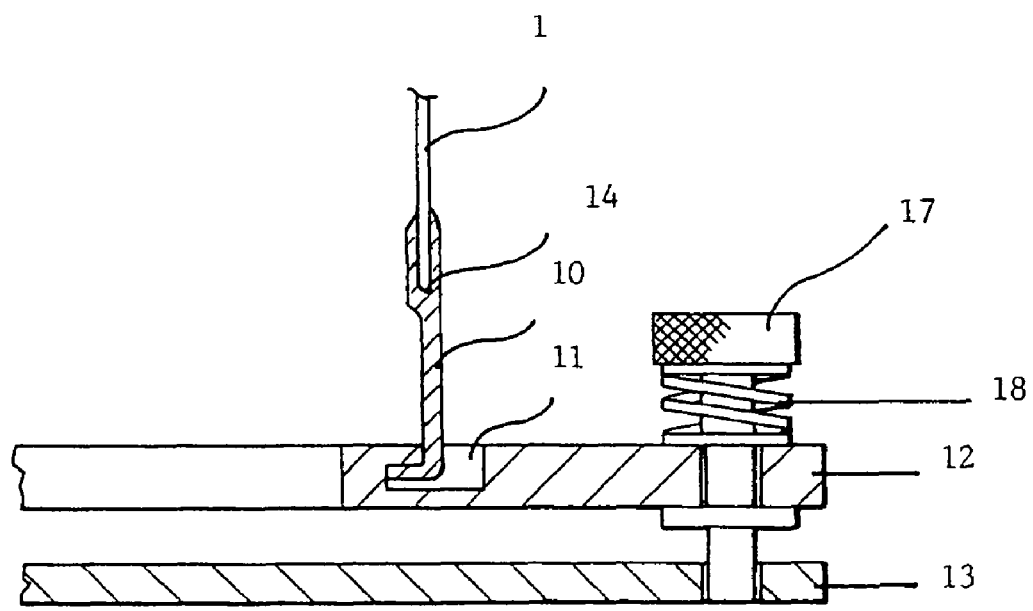

In the embodiment shown in FIG. 6, opposite longitudinal edges 15 of the template 1 are each connected to connecting means 10. The connecting means 10 are provided to be releasably fixed in a groove 11 provided in the fixation plate 3. The fixation plate 3 comprises a top plate 12 and a bottom plate 13, the top plate 12 being displaceable towards and from the bottom plate 13, in view of increasing or decreasing the pulling force exerted by the template 1. In the case shown in FIG. 6, the distance between the top and bottom plate is continuously variable by means of screws 17, the position of the top plate being fixed with respect to the screw 17 by means of a resilient member 18. The spring constant of the resilient member 18 will usually be selected so as to obtain the desired fixation force.

If so desired the distance between the fixation plate 3 and the template 1 may also be varied by positioning on top of the fixation plate 3 an expandable member, which is provided to support the patients' head and/or the head and neck support 2. Or else, the head and neck support may be made of an expandable material.

The template 1 will generally be made of a thermoplastic material, for example a thermoplastic polyolefin, poly-є-caprolacton, polyurethane, or other types of polyester. However, a material having a different shrinking coefficient upon cooling and crystallisation may also be used. The shrinking force exerted by the template during cooling and crystallisation, which mostly is isometric, may be measured by means of the device disclosed in Belgian patent application No. 2002/05012808.

The patient immobilisation assembly of this invention presents the advantage that it does not add any parts to the existing systems, which otherwise could interfere with the radiation directed to the patient. It is of utmost importance that radiation originating from various directions can be directed to the patient, to allow for an optimum treatment. With the presence of interfering parts, it may be required to adapt the instrumentation and planning of the treatment. This is unwanted.

The invention also relates to the template, the above described fixation plate, expandable fixation plate, expandable template, expandable spacer, expandable connecting means and expandable head and neck support for use with the above described assembly.

The invention claimed is:

1. A non-invasive patient immobilisation assembly for immobilising a body part of a patient and for at least temporarily fixing the position thereof, wherein the immobilisation assembly comprises
   a rigid template made of a thermoplastic material, which template is thermoformed or otherwise moulded in such a way that an inner surface has a shape adapted to conform to, and during use, to contact the body part to be immobilised along a contact surface area between the template and the body part, which contact surface area corresponds to at least part of the inner surface of the template,
   a fixation plate,
   connecting means for connecting the template to the fixation plate in view of fixing the position of the template and the body part with respect to the fixation plate, wherein the template is provided to exert, during use, a fixation force of a preset value on the body part covered by it along the contact surface area, by exerting a pulling force pulling the body part towards the fixation plate with the aim of restraining the displacement of the body part within the template within defined limits, and
   means for adjusting the fixation force exerted by the template to the preset value.

2. The assembly as claimed in claim 1, wherein the fixation force exerted by the template is about 75-200 N.

3. The assembly as claimed in claim 1, wherein the means for adjusting the fixation force are adjustable in a continuous or discontinuous manner.

4. The assembly as claimed in claim 3, wherein the means for adjusting the fixation force provide a stepwise adjustment of the fixation force.

5. The assembly as claimed in claim 1, wherein the template comprises at least one edge, wherein the connecting means connecting the template to the fixation plate are connected to the at least one edge, and wherein the pulling force is exerted to the at least one edge of the template.

6. The assembly as claimed in claim 1, wherein the means for adjusting the fixation force exerted by the template comprise means for varying the distance between the template and the body part to be immobilised.

7. The assembly as claimed in claim 6, wherein the means for adjusting the fixation force comprise means for displacing the template with respect to the body part, in view of varying the distance of the template with respect to the body part to be immobilised.

8. The assembly as claimed in claim 1, wherein the fixation plate comprises a top surface and bottom surface, wherein the template is connected to the top surface, and wherein said means for adjusting the fixation force includes means for moving the top surface with respect to the bottom surface.

9. The assembly as claimed in claim 1, wherein the fixation plate comprises a top surface and bottom surface, wherein the template is connected to the bottom surface, and wherein said means for adjusting the fixation force includes means for moving the bottom surface with respect to the top surface.

10. The assembly as claimed in claim 1, wherein the assembly comprises a support, the support being provided for positioning on top of the fixation plate in view of supporting the body part to be immobilised, and wherein the means for adjusting the fixation force comprise means for varying the position of the support with respect to the template.

11. The assembly as claimed in claim 1, wherein the assembly comprises a support for supporting the body part to be treated, the support being positioned independently of the fixation plate, and wherein the means for adjusting the fixation force comprise means for varying the position of the support with respect to the template and/or the fixation plate.

12. A non-invasive immobilisation assembly for immobilising a head of a patient and for at least temporarily fixing the position thereof, wherein the immobilisation assembly comprises a rigid template made of a thermoplastic material, which template is thermoformed or otherwise moulded in such a way that an inner surface has a shape adapted to conform to, and during use, to contact at least part of the head to be immobilised along a contact surface area between the template and at least part of the head, which contact surface area corresponds to at least part of the inner surface of the template, a fixation plate, connecting means for connecting the template to the fixation plate in view of fixing the position of the template and the head with respect to the fixation plate, wherein the template is provided to exert, during use, a fixation force of a preset value on the part of the head covered by it along the contact surface area, by exerting a pulling force pulling the head towards the fixation plate with the aim of restraining the displacement of the head within the template within defined limits, and means for adjusting the fixation force exerted by the template to the preset value.

13. The assembly as claimed in claim 12, wherein the device comprises a head and neck support for supporting the head and neck of a patient.

* * * * *